United States Patent [19]

Wikséll et al.

[11] Patent Number: 4,846,196

[45] Date of Patent: Jul. 11, 1989

[54] METHOD AND DEVICE FOR THE HYPERTHERMIC TREATMENT OF TUMORS

[76] Inventors: Hans O. T. Wiksell, S-183 44; Gert J. Boëthius, S-183 63, both of Täby, Sweden

[21] Appl. No.: 7,026

[22] Filed: Jan. 27, 1987

[30] Foreign Application Priority Data

Jan. 29, 1986 [SE] Sweden ............................... 8600387

[51] Int. Cl.[4] .......................... A61N 1/06; A61N 1/32

[52] U.S. Cl. .................................... 128/784; 128/736; 128/804

[58] Field of Search ............... 128/784, 785, 804, 422, 128/736

[56] References Cited

U.S. PATENT DOCUMENTS

| | | | |
|---|---|---|---|
| 4,016,886 | 4/1972 | Doss et al. | 128/784 |
| 4,448,198 | 5/1984 | Turner | 128/804 X |
| 4,572,214 | 2/1986 | Nordenstrom et al. | 128/785 |

FOREIGN PATENT DOCUMENTS

| | | | |
|---|---|---|---|
| 0115420 | 8/1984 | European Pat. Off. . | |
| 1143937 | 2/1963 | Fed. Rep. of Germany | 128/804 |
| 8502779 | 7/1985 | World Int. Prop. O. | 128/804 |

*Primary Examiner*—Lee S. Cohen

*Attorney, Agent, or Firm*—Armstrong, Nikaido, Marmelstein, Kubovcik & Murray

[57] ABSTRACT

A method and device for hyperthermic treatment of tumors. At least two electrodes connected to an RF source of energy are brought into contact with the patient's body for transmission of RF energy to the tumor area. One of the electrodes constitutes a treatment electrode system, shaped with an external surface the same size as the tumor area and intended to be applied therein, and the other electrode constitutes an indifferent electrode, considerably larger in area, intended to be in external contact with the skin of the body. The treatment device comprises a generator with low impedance, low generator voltage and greatest possible output.

9 Claims, 4 Drawing Sheets

8

14

2

10

CONTROLLER

4

6

METHOD AND DEVICE FOR THE HYPERTHERMIC TREATMENT OF TUMORS

BACKGROUND OF THE INVENTION

1. Field of the Invention

The present invention relates to a method and device for hyperthermic treatment of tumors, more particularly to the hyperthermic treatment of tumors using a device comprising two electrodes connected to an RF source of energy and intended to be brought into contact with the patient's body for transmission of RF energy to the tumor area.

2. Description of Related Art

It is well known that hyperthermic treatment can have a beneficial effect on tumors. Descriptions of the technology have been available since the nineteenth century and it has gained ground noticeably over the last decade. Hyperthermic treatment is now established clinical routine for certain types of tumor diseases in the United States. The treatment may be local or entail heating the entire body and is based on the fact that tumorous cells are more sensitive to heat than healthy cells in certain situations. The temperatures relevant for local hyperthermy are generally in the range of 42°–44° C. Within this range hyperthermic treatment can kill tumorous cells whereas healthy cells will survive. Exposure times are usually from some ten minutes up to several hours or even days. The treatment is frequently repeated several times and is frequently combined with other forms of treatment such as surgery, treatment with ionizing radiation and cytostatic treatment.

The main problem will all local hyperthermic treatment, particularly the treatment of brain tumors, is the difficulty of effecting well defined and well controlled heating of exactly the relevant volume and achieving appropriate temperature gradients without the risk of producing areas with too high temperature, known as hot spots.

Several different methods are known for generating local hyperthermy, e.g., the use of heat-exchangers connected to the body in various ways, electrically heated filaments of various design for insertion into the body, dielectric heating ("short-wave"), the insertion of needle electrodes into a tumor area and connecting RF energy to these needle electrodes, conventional diathermy or monopolar or bipolar type, and microwave heating. For example, European Application No. 0 115 420 discloses a device for hyperthermia comprising a first electrode adapted to be disposed in a tract organ and a second electrode adapted to be disposed on the outer circumference of the human body so as to generate a spatially inhomogeneous electric field within the living body in cooperation with the first electrode so that a part of the living body near the first electrode may be heated more strongly than a part of the living body near the second electrode.

The present inventors previously developed a system for local hyperthermy for the treatment of brain tumors, etc., and have clinically tested the system. The prospects for patients suffering from gliomatous tumors in the brain are extremely bleak and new, unconventional therapy is therefore necessary to deal with this disease. There are some 400 cases a year in Sweden.

This clinically tested method is based on the use of a wire system comprising a DC filament and temperature sensors built into an extremely flexible casing of thin silicone rubber tubing. The tube is prepared before treatment is to be carried out and must therefore have a "finished" length and fulfill all the requirements of sterility, safety, etc. The tube is then inserted, assuming the tumor has a cavity, using stereotaxic neurosurgical methods, for instance. In other cases it can be inserted when removing the central part of the tumor by surgery. The important thing is for the tube to be wound into a ball in the cavity, thus exposing a large area to heat but being small in volume. The tube forming the ball is also used as conductor, and thus passes through the brain and out through a tunnel to an external contact. During treatment the system is connected to a control and power supply unit via this contact. The filament is heated and the temperature response can be detected via the built-in sensors. At the beginning of the heating process a cascade effect occurs in the system so that heating is greatest in the area where the tube is wound into a ball, i.e., where the density is greatest. The resistance in this part of the filament thus increases, causing even greater heating of just this part of the system.

It has been possible to achieve a relatively good hyperthermic thermal image using this method. However, it does have some weaknesses. A relatively high temperature is attained in the central part of the ball, for instance, and the heat is transported to the growth zones of the tumor and to surrounding tissue including any diffusely spread tumor cells primarily by way of conductor transport (heat diffusion). The drawback here is that a rather high central temperature must be reached in order to achieve a therapeutic temperature in regions surrounding the electrode, and this causes undesired side effects such as oedema. In animal experiments a temperature of 43° C. has been documented at a distance of 4 mm from the heating system, with a central temperature of 50° C. Such results show too great a thermal gradient.

The problem to be solved by the present invention is to achieve a device for hyperthermic treatment of tumors in which the heating is well controlled, ensuring that exactly the desired volume is heated to precisely the desired over-temperature as discussed above, and so that a relatively slight temperature gradient is achieved, i.e., relatively large volumes are heated to a moderate over-temperature. The situation aimed at is to achieve a temperature of approximately 42.5° C. at a distance of a centimeter or so from the electrode without the central temperature becoming too high, i.e., to eliminate the above-mentioned drawbacks of high central temperature and abrupt temperature gradients.

SUMMARY OF THE INVENTION

According to the present invention, controlled hyperthermic treatment of tumors is obtained by a method wherein a tumor is contacted with a treatment electrode having a relatively large external surface area substantially equal to the tumor area and RF energy is transmitted to the tissue immediately surrounding the electrode at a sufficiently low impedance to provide controlled heating of the tissue.

The device according to the present invention for the controlled hyperthermic treatment of tumors comprises two electrodes connected to an RF energy source and adapted to be brought into contact with a patient's body for transmission of RF energy to the tumor area. One electrode is a treatment electrode having a relatively large external surface area that is about the same size as the tumor area and adapted to be brought into contact therewith. A second electrode is an indifferent electrode adapted to be in external contact with the skin of the body of the patient. The RF energy source comprises a generator capable of low impedance and low generator voltage and very high output and capable of handling a high degree of maladjustment.

In a preferred embodiment the treatment electrode is adjustable in size, or expandable, such that it can be expanded after insertion into a tumor to assume the size of the tumor area.

DESCRIPTION OF THE DRAWINGS

FIG. 8 shows a temperature sensor element.

FIG. 9 illustrates an arrangement for insertion of the temperature sensor.

DESCRIPTION OF PREFERRED EMBODIMENTS

Figure 1:
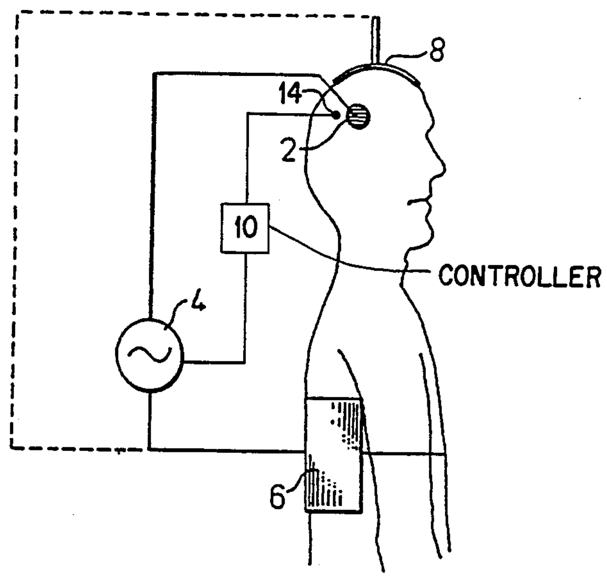
FIG. 1 is a schematic view illustrating the use of the method and device according to the present invention for treating a brain tumor in a patient.

The device according to the present invention is based on utilizing the tissue of the tumor itself as a heating element, i.e., the heat is generated in the actual tissue where the over-temperature consequently occurs. The technology can be explained with the aid of the following models:

The tissue can be considered as a three-dimensional grid or electrical network of finite cubes with sides offering resistance with relatively low numerical value. Some components of inductive and capacitive type are also included in the resistance. It is also important to note that the sides of the grid do not have exactly homogeneous conductivity values, but may fluctuate. One can therefore speak of different conductivity distribution in the tissue from the geometrical aspect. The geometric shape and extension of the "body" are also significant.

In conventional RF heating such small electrode surfaces have been used that the total supply impedance is relatively high in relation to the grid impedance of the tissue according to the above model. That is to say, most of the voltage applied will be in the junction between electrode and tissue. The entire grid thus behaves as a homogeneous volume and only the areas extremely close to each electrode will be heated. Due to the non-linear phenomenon, this may result in the RF energy supplied modifying the electrical properties of the tissue. A certain change occurs in the liquid content, for instance, which increases the resistivity and produces local heating in the immediate area of the electrode. The phenomenon is particularly noticeable when using monopolar diathermy to effect stypticity and coagulation or during surgery when an extremely local process occurs at the contact point for the hand-piece electrode, giving rise to a pronounced change in the liquid content and, possible, charring of the tissue. A large potential gradient is thus obtained at the electrode, while the remaining grid points receive substantially the same potential, i.e., no heating occurs through forced current distribution over the grid system as is described below in connection with the present invention.

In the present invention an extremely large area is utilized for the treatment electrode, resulting in extremely low supply impedance between this and the indifferent electrode, which has an area several times larger than the treatment electrode. It is not possible to specify the minimum surface area of the treatment electrode because the area will vary depending on the size of the tumor. In most cases the tumor will have a diameter of 0.5–1 dm. The area of the indifferent electrode will typically be from about 2 up to several $dm^2$.

In experiments carried out in an autopsy department using a treatment electrode in the form of a sphere 25 mm in diameter, a typical supply impedance of 30 ohm was measured at a frequency of 2.0 MHz. Corresponding values noted when using "needle electrodes" of the type used in previously known RF heating methods and inserted in "small" tumor areas, were in the range of 10–100 Kohm. In all likelihood the same values would be obtained on a living patient. With the device according to the invention, thus, a supply impedance is obtained which is thousands of times lower than when using needle electrodes in accordance with conventional technology. This reduction in impedance is of decisive significance in penetrating the grid described in the model above.

With the device according to the invention, therefore, such a large current is "forced" onto the tissue matrix (e.g., a value of about 3 $A/cm^2$) that the voltage is distributed over a large area, following laws of potential similar to those applicable to the flow of groundwater in porous ground layers. Contrary to the case when using conventional RF heating using small electrode surfaces as described above where a covering of burned material is formed on the electrode and insulates the electrode, the device according to the invention avoids the non-linear phenomenon—difficult to control—since the impedance is independent of the power because there is a "sufficiently" large conducting area for the current. Furthermore, the voltage applied will be substantially in the tissue itself. The differences in potential thus appearing in the tissue give rise to a unique heating process and produce a situation extremely close to the ideal for local hyperthermic treatment of a relatively large area in and surrounding a tumor. The characteristic feature is that the actual central tumor area, which in the case of brain tumors may be large and cystic and constitute a substantially spherical volume several cm in radius, is not actively heated at all (since all grid points in the model above receive the same electric potential). On the other hand, a current distribution is achieved in the areas surrounding the central part, constituting both the growth zone of the tumor and the surrounding, substantially healthy tissue which may contain tumor cells spread diffusely and which are, therefore, potentially extremely dangerous. This current distribution spontaneously gives a thermal image having a low central temperature and an extremely slight gradient over a large volume and thus the desired type of heating with good therapeutic over-temperature over an extremely large area without the high central over-temperature which would be required for efficient diffusion if heat conduction were to be used for treating a relatively large tumor area. With the device according to the invention, therefore, the desired thermal image is achieved since the tumor tissue itself behaves as a heat element and generates heat exactly at the place required without the need for thermal transport.

The heating characteristics of the method according to the present invention were studied with the aid of experimental phantom models and thermocameras. Thereafter empirical and theoretical models were developed and then experiments carried out in vitro and later in vivo on animals. No histological damage besides the desired thermal effects could be detected in these latter experiments, despite the extremely high currents used.

Animal experiments have thus proved that the method can be utilized without side effects or discomfort for the patient and that temperatures in the vicinity of 43° C. can be achieved at a distance of several cm from the central body of the tumor where the electrode is applied.

Initially it was feared that uneven conductivity in the treatment area might entail risks of uncontrollable hot spots in sensitive structures such as at the exit of the cranial nerves into the cranium. However, the experiments indicated that such is not the case. On the contrary, an extremely satisfactory thermal image can be achieved without hot spots.

There are several other positive factors associated with the method. Circulation is modified, leading to a favorable cooling effect in many cases. Admittedly the tumor tissue often contains more blood vessels than healthy tissue, but circulation is considerably less efficient and since circulation is of decisive significance to cooling, the tumor tissue will be heated more than the healthy tissues. This phenomenon has been studied by measuring both the temperature and the active power input as a function of time during the treatment.

White brain matter containing myelin also appears to be heated somewhat more due to its typical conductivity and lower blood circulation. This has a positive effect on the treatment of glioma which grows more easily through white matter. White matter also appears to be somewhat more sensitive to heat than grey matter.

One pre-requisite for achieving the desired thermal image is thus that the total supply impedance is extremely low so that the grid in the above model is placed under voltage with varying potential and typical equipotential lines. This demands treatment apparatus enabling RF supply with extremely low impedance, the voltage supplied being unaffected by variations in load. Considerable maladjustment is possible and considerable output must be available from the generator, combined with the opportunity to measure current, voltage and phase angle. Furthermore, a type of infrastructure must be achieved for the potential distribution. The following distribution may be mentioned, measured on dogs, with the indifferent electrode applied on the dog's abdomen and the treatment electrode in the brain: indifferent electrode/adjacent abdominal tissue approximately 5-10%; abdomen/head, particularly neck region, approximately 60% (this high proportion of the total energy supplied is of no significance, however, since it acts over a very large volume) and 30% for the head, particularly the brain. This infrastructure may in turn create a certain tendency to asymmetry in the thermal image and this has been utilized to further improve the shape of the thermal image. This is done by using an additional indifferent electrode which, possibly with some voltage division, is placed in contact with the skin on the top of the head.

In view of the complexity of the human body it is often difficult in advance to theoretically calculate the heating image of a certain electrode arrangement. In practice, therefore, it may be advisable to place a container around the lower part of the head and neck, fitting tightly against the shoulders and containing a suitable liquid, e.g., a salt solution, which will show substantially the same electrical properties as the human body. A simpler total geometry is thus obtained which facilitates predetermination of the thermal image. Such a procedure also has the advantage of eliminating the risk of unpleasant or injurious heating of the neck as a result of the reduced cross-sectional area.

With the extremely lower impedances discussed above which are required for the device according to the invention, it is important that the conducting area in the treatment electrode and its conductor is such that this impedance (the inner impedance of the electrode and connections to the electrode) only constitutes a fraction of the total impedance. Otherwise the electrode parts will be heated too much. This also places specific demands on both electrode and conductor. A spherical metal electrode with relatively large dimensions has been tested, as well as other versions of a system using a ball of metal wire. The latter offers the advantage of allowing removal of the system without resorting to surgery, by simply withdrawing the wire.

According to a preferred embodiment of the device according to the present invention, the treatment electrode consists of a "loose" conducting material such as aluminum pellets, gold-plated to give good electrical contact and contained and applied in a sleeve or pocket of large-mesh net material such as nylon, to enable good galvanic contact with the surrounding body tissue. The pellets may be up to a few mm in diameter. Such a treatment electrode enables the tumor cavity to be efficiently filled with the electrode. The sleeve or pocket is inserted into the tumor cavity first and thereafter the pellets are inserted through a tube applied in a channel close to the tumor. After the treatment the pellets are withdrawn through the tube, followed by the sleeve or pocket, thus avoiding re-operation.

According to another embodiment of the device according to the present invention, the treatment electrode comprises a flexible conductor, preferably a metal wire, which can be inserted into a tumor and wound up there to form a ball. When treating brain tumors, the wire is inserted through a small hole drilled in the skull so as to wind itself into a ball inside the tumor, which is sometimes hollow even before the operation.

According to a third embodiment of the device according to the present invention, the treatment electrode comprises an inflatable balloon-like structure which on its outside is provided with an aluminum cover. The balloon-like electrode may be placed within the tumor area and thereafter inflated, or "blown up", to fill the whole treating area.

The useful frequency range is relatively large. It is often stated in relevant literature that the frequency is of significance to the heating obtained, but this is not the case for the frequency ranges tested here. However, the following must be observed when selecting the frequency: it must not be so low as to cause nerve irritation, muscle stimulance or interaction with the electrical system inherent in the brain. The limit for this lies at frequencies below about 1 KHz. The use of too high frequencies, above 50 MHz, gives rise to another type of problem, that of dosage difficulties. These appear when the wave-length of the RF energy supplied approaches the magnitude of the physical dimensions of the heated area and of the electrode system and conductor. Standing waves appear at high frequencies, which complicate dosing and easily result in unreliable localization of the heating and general RF transmission difficulties. Frequencies of about 1 MHz have been used hitherto and the experiments have therefore been carried out in a Faraday cage in order to avoid radio disturbances. It should, however, be noted that a low antenna effect is obtained at around 2 MHz since the conductors used are short in relation to the antenna effect (wavelength/4).

For lower frequencies direct contact is required between the body and the electrodes, but with higher frequencies a capacitive connection is also possible. However, in the latter case, as with the auto-conductivity of the electrode, the capacitive reactance obtained may be permitted to constitute only a fraction of the total impedance of the whole system, as described above.

It is naturally of great importance to be able to accurately follow the responses to input. For this reason, according to the invention one or more temperature sensors are arranged in the vicinity of the treatment electrode, to monitor the temperature in the treatment area. Specially developed subminiature platinum type temperature sensors are preferably used. The problem is to avoid as far as possible interaction between temperature sensors and the RF field, so that the temperature image can be measured as accurately as possible with a minimum of disturbance phenomena. Thus the sensor may not disturb the RF field, nor may the RF field disturb the sensor. The temperature sensor in the device according to the invention preferably consists of small chips coated with a thin layer of platinum. Using a laser, the metal layer is cut to a Z-shape giving suitable resistivity. The platinum chips are supplied with voltage via a system of compensation conductors, and the resistance is measured using compensation conductors with high impedance so that the voltage drop will be negligible, as described below. This gives high measuring accuracy. The small dimensions of the platinum chips also enable the interaction mentioned above to be reduced to a minimum.

Generally a system having three strategically placed sensor points is used. The sensors are spaced from each other in a protruding tube which will penetrate the tissues near the electrode, and the position of the sensors is determined by X-ray. The sensor points may also be provided with X-ray contrast for localization. In one embodiment of the device according to the present invention, the treating electrode is a metal ball having a silicone tube protruding from the ball and containing three temperature sensors spaced from each other.

A new technique has also been studied for three-dimensional, non-invasive measurement of the thermal image. A blood-brain boundary exists in the brain, for instance, which is broken down by over-temperature. When the blood-brain boundary has been eliminated, intravenously injected X-ray contrast is able to fill the heated area and the image can be studied while hyperthermic treatment is in progress using modern imaging technology such as computer tomography, magnetic resonance or with the aid of a positron camera.

To summarize, it can therefore be established that with the device according to the present invention, geometrically controlled heating of the brain tissue is possible by generating a specific current-density distribution by means of a suitable electrode which is inserted in the tumor area and supplied with electric RF energy in a specific manner. Both the extent of the heated area and its temperature gradients can be controlled by varying the location of the electrodes, their design or by the use of several electrodes.

The shape and extent of the heated area can also be influenced by the design and location of the indifferent electrode. According to an advantageous embodiment of the device according to the invention, this electrode comprises a metal foil, such as an aluminum foil, of a relatively large area, which is placed in contact with the patient's trunk and/or in contact with the patient's head. Alternatively this electrode may comprise two metal foils applied to both places.

Besides brain tumors, for which extremely great precision is required in the treatment, the device according to the invention is also very suitable for treating tumors in other cavities of the body such as intestinal tumors, tumors in the bladder, as well as for treatment of tumors in the liver or pancreas. Treatment electrodes specially designed for the purpose are possible, such as in the form of a metal ball or a metal cylinder. Cylindrical electrodes may be suitable for treating deep cavities, such as disseminated rectal cancer.

The temperature sensed is preferably fed back to the energy source with the aid of suitable control equipment, in order to control the power supplied depending on the temperature sensed, thus maintaining the temperature in the treatment area at a constant predetermined value.

Other advantages of the device according to the invention are that the treatment is performed while the patient is fully conscious, enabling conversation with the patient so that the treatment can be discontinued should side-effects appear or the patient experience great discomfort. Normally, the treatment is substantially painless for the patient.

The invention will now be described in more detail with reference to the accompanying drawings illustrating embodiments of the device according to the invention.

FIG. 1 shows a conductor wire inserted in the tumor cavity, to form a treatment electrode 2 in the form of pellets, for instance, in a net material, or in the form of a ball of wire. The pellets may be of aluminum plated with gold to give good electrical contact, and enclosed in a pocket or sleeve of relatively large-mesh net material, e.g., nylon. The electrode 2 is connected to an RF source 4, the other pole of which is connected to an indifferent electrode 6, in the form of a relatively large aluminum foil 6, applied on the skin of the patient's back.

If a ball of wire is used as the treatment electrode, the total length of wire is suitably 80 cm and about 50–60 cm of this, i.e., 60–75%, is normally inserted into the tumor cavity, essentially filling it. The length of wire will vary, of course, depending on the size of the tumor cavity to be filled.

The wire itself which is inserted into the tumor cavity to form the treatment electrode 2 consists of a conducting wire, such as a copper wire. The diameter of the wire should be sufficiently small to facilitate formation of the ball of wire in the tumor cavity. It is also possible to use an insulated wire, for instance a metal wire in a thin silicone rubber tube, capacitively connected to the surrounding tissue.

The energy distribution in the treatment area can be varied by varying the location and shape of the indifferent electrode. It can thus be applied on the patient's head as indicated in FIG. 1 at 8.

The indifferent electrode may also include several contact plates or foils, located at different points on the body and having variable resistance to earth. This enables the current distribution to be controlled as desired with great accuracy.

The indifferent electrode may also consist of a liquid electrode, simply by immersing the patient in a bath of suitable conducting liquid. The indifferent electrode will thus be in contact with most of the patient's body.

As mentioned above the RF source 4 comprises a generator with large available output and low output impedance. The generator 4 should be capable of supplying up to several hundred W since maladjustment may sometimes be considerable due to reflection, for instance. About 10–200 W of active power is typical of the power utilized with a low generator voltage. The output impedance is in the order of magnitude of 10 to 100 ohms. The frequency of the generator 4 may not be too low since this may give rise to undesired nerve stimulance as mentioned above, nor too high since this will give rise to uncontrolled conditions and standing waves without controlled energy transfer to the tumor tissue. Suitable frequencies may be between 1 and 50 MHz.

Figure 2:
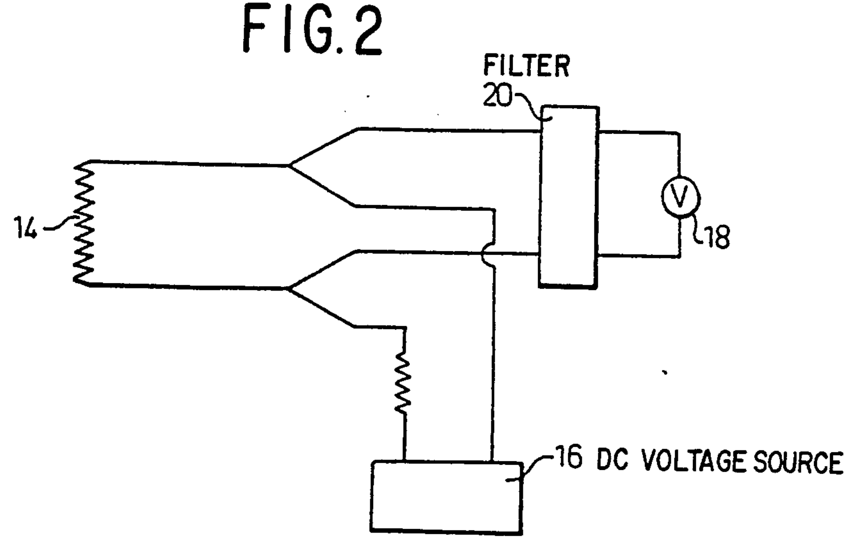
FIG. 2 shows a principle diagram of an embodiment of a temperature measuring device useful in the method of the present invention.
Figure 1A:
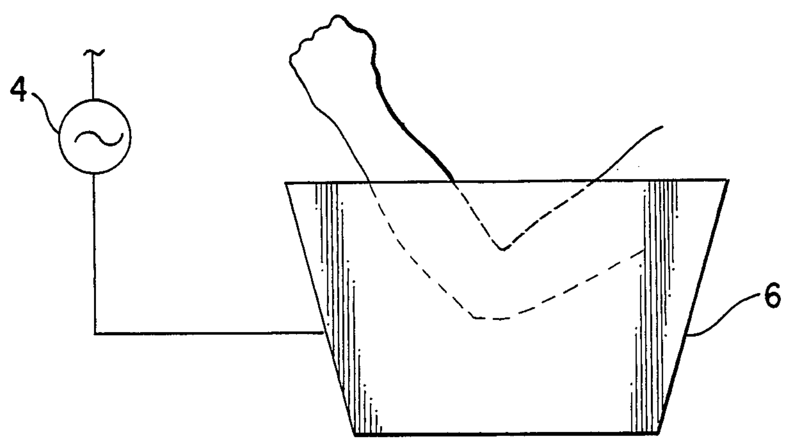
FIG. 1*a* illustrates an embodiment of the indifferent electrode.

Referring to FIG. 2, the temperature sensor element 14 consists of a platinum wire, for instance, which is Z-wound on the surface of an extremely small chip. This element is produced by vaporization of a platinum foil on the chip, a Z-wound foil then being cut with a laser as described above. The voltage over the platinum wire 14 is measured by a direct voltage from a direct voltage source 16 and the voltage over the wire 14 is measured using a voltmeter 18 having high internal resistance, for example, a voltmeter based on an A/D converter. To minimize interaction with the RF field, as discussed above, a disturbance filter 20 is connected between the voltmeter 18 and the sensor wire 14.

Using suitable control equipment, 10 the temperature measured can be used for direct control of the power generator 4 so that this emits a power sufficient to maintain the temperature in the tumor area at a specific value.

Control may be effected from various temperature sensors applied in the treatment electrode, their signals being fed into a computer. This computer can check that no point has too high a temperature. It can also estimate the geometry of the temperature image since it is able to calculate the shape empirically from known relationships. It can also measure input (including the phase angle between current and voltage) and compare this with the prevailing temperature. This enables conclusions to be drawn concerning the circulation. An adaptive control algorithm can also be used enabling successively improving control.

As mentioned above, one advantage of the method described in the relatively slight temperature gradient, i.e., relatively uniform heating of a large area without a high central temperature. This is illustrated qualitatively in FIG. 4.

In certain cases, however, it may be desirable to produce larger temperature gradients in the tissues surrounding the electrode. This can be achieved by using electrode arrangements similar to that described above with an insulated resistance wire, with direct voltage. Such a treatment electrode will then serve as a heat source from which heat is transmitted to the surrounding tissue through conductors. This gives relatively high heat in the central part of the tumor where the electrode is placed, but the temperature drops rapidly outside the electrode.

Figure 3:
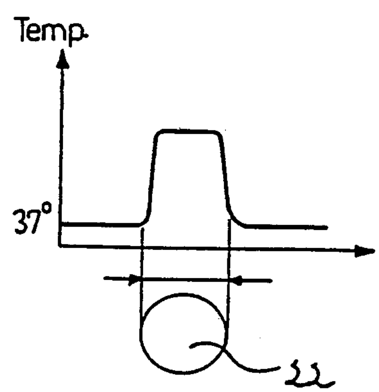
FIGS. 3 and 4 are graphs showing the temperature distribution obtained in the treatment area when using a treatment electrode having a relatively large surface area supplied from a DC and RF source, respectively.
Figure 4:
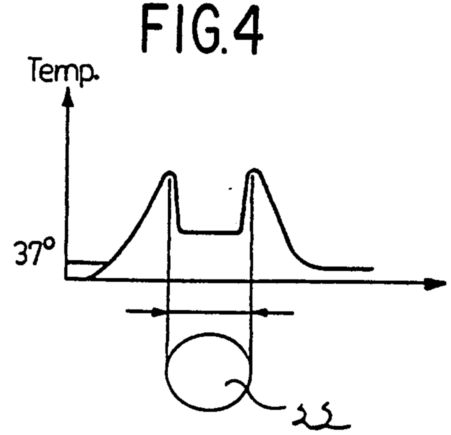

FIGS. 3 and 4 show qualitatively the spacial temperature distribution achieved when supplying the treatment electrode with direct voltage, FIG. 3., or with radio-frequency alternating current, FIG. 4. In FIG. 3 heating is relatively intense in the central part 22 where the treatment electrode is located, with a large temperature gradient outside, whereas in FIG. 4 the temperature in the central part is moderate and the temperature gradient outside the treatment electrode is smaller.

In some cases it may be advisable to combine these two methods.

The device according to the invention can also be used for "post-treatment" of an operated tumor, for treatment of the exterior of the tumor where effective surgery is often difficult or impossible. The power supplied may be RF or DC, or a combination of these, depending on the temperature distribution desired.

Figure 5:
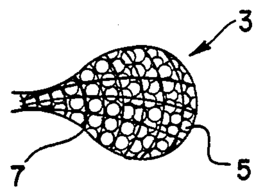
FIGS. 5, 6 and 7 illustrate embodiments of the treatment electrode according to the method and device of the present invention.
Figure 6:
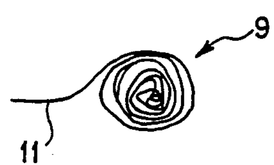
Figure 7:
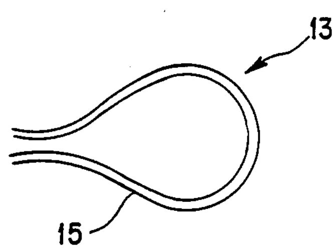

FIGS. 5, 6 and 7 illustrate various embodiments of treatment electrodes useful in the method and device according to the present invention. The electrode 3 shown in FIG. 5 includes a plurality of metal pellets 5 coated with a metal of high conductivity, e.g., aluminum pellets plated with gold. The pellets 5 are contained in a mesh sleeve or pocket 7 of nylon or other suitable flexible material. The combined use of the pellets and flexible sleeve allow the electrode 3 to completely fill and assume the shape of the tumor cavity in which it is used.

FIG. 6 shows a treatment electrode 9 in the form of a ball. The electrode comprises a fine metal wire 11 such as copper which has been wound into a ball of appropriate size.

FIG. 7 shows an inflatable balloon-type treatment electrode 13. The electrode comprises a balloon, or bag, 15 of a flexible film coated with a metal such as aluminum. The electrode can be inserted into a tumor cavity and then inflated to fill and take the shape of the cavity.

Although the method and device for the hyperthermic treatment of tumors according to the present invention has been described in conjunction with certain preferred embodiments, there is no intent to limit the invention to these embodiments. Instead, the invention is intended to include all those embodiments within the scope and spirit of the appended claims.

We claim

1. A device for hyperthermic treatment of a tumor comprising at least two electrodes adapted to be brought into contact with a patient's body for transmission of RF energy to the tumor area, at least one of said electrodes being a treatment electrode comprising an inflatable balloon having an external surface coated with a conductive metal, and means to expand said inflatable balloon to have an external surface area substantially the same size as the tumor area and adapted to be brought into contact therewith, at least one other electrode being an indifferent electrode larger in area than said treatment electrode and adapted to be in external contact with the skin of the body, and an RF energy source connected to said at least two electrodes.

2. A device according to claim 1, wherein the indifferent electrode comprises a metal foil adapted to be placed against the skin over a part of the patient's trunk or in contact with the skin on the patient's head.

3. A device according to claim 1, wherein the indifferent electrode comprises two metal foils, one of which is intended to be brought into contact with the skin of the patient's trunk and the other with the skin of the patient's head.

4. A device according to claim 1, wherein the indifferent electrode comprises a plurality of contact plates or foils having variable resistance to earth to permit control of the current distribution.

5. A device according to claim 1, wherein the indifferent electrode is a liquid electrode.

6. A device according to claim 1, further comprising: at least one temperature sensor adapted to be in contact with the tumor area for temperature sensing, said temperature sensor comprising a temperature-sensitive platinum wire wound onto a chip, a direct voltage source connected thereto and a voltmeter with a high input impedance which measures the voltage across the wire; and means for controlling the output of the RF energy source in response to the sensed temperature.

7. A device according to claim 6, wherein the temperature sensor is in the form of a ball applied in a sleeve or pocket.

8. A device according to claim 1, wherein the frequency of the RF energy source lies within the range of 10 kHz–100 MHz.

9. A method for controlled hyperthermic treatment of a tumor having a central cavity comprising inserting into the tumor an inflatable treatment electrode having an external surface area substantially equal to the area of the tumor defined by the cavity, expanding said electrode to assume the shape of the cavity and supplying RF energy to the tumor through the treatment electrode at a low output impedance such that controlled heating is generated in the tumor using the tissue of the tumor as a heating element.

* * * * *